(12) United States Patent
Matsuhashi

(10) Patent No.: US 12,714,852 B2
(45) Date of Patent: Aug. 25, 2026

(54) MASSAGE DEVICE

(71) Applicant: Naoko Matsuhashi, Tokyo (JP)

(72) Inventor: Naoko Matsuhashi, Tokyo (JP)

( * ) Notice: Subject to any disclaimer, the term of this patent is extended or adjusted under 35 U.S.C. 154(b) by 0 days.

(21) Appl. No.: 18/286,995

(22) PCT Filed: Feb. 9, 2022

(86) PCT No.: PCT/JP2022/005119
§ 371 (c)(1),
(2) Date: Oct. 13, 2023

(87) PCT Pub. No.: WO2023/152827
PCT Pub. Date: Aug. 17, 2023

(65) Prior Publication Data

US 2024/0189586 A1 Jun. 13, 2024

(51) Int. Cl.
*A61N 1/14* (2006.01)

(52) U.S. Cl.
CPC .................................... *A61N 1/14* (2013.01)

(58) Field of Classification Search
CPC ............................ A61N 1/14; A61N 361/212
See application file for complete search history.

(56) References Cited

FOREIGN PATENT DOCUMENTS

| | | | | |
|---|---|---|---|---|
| CN | 108815703 A | * 11/2018 | A61H 39/002 |
| CN | 111617381 A | * 9/2020 | |
| DE | 3815593 A1 | * 11/1989 | A61N 2/00 |
| JP | S51110665 | 9/1976 | A61N 2/00 |
| JP | H73643 | 1/1995 | A61N 39/08 |
| JP | 201533513 | 2/2015 | A61N 1/14 |
| JP | 2020168060 | 10/2020 | A61N 1/14 |
| JP | 2020168060 A | * 10/2020 | |

OTHER PUBLICATIONS

International Search Report with English translation and Written Opinion issued in PCT/JP2022/005119, dated 9 pages.
International Preliminary Report on Patentability issued in PCT/JP2022/005119, dated Aug. 6, 2024, English translation, 7 pages.

* cited by examiner

*Primary Examiner* — Crystal L Hammond
*Assistant Examiner* — Samantha L Faubert
(74) *Attorney, Agent, or Firm* — HAYES SOLOWAY P.C.

(57) ABSTRACT

A massage device is provided capable of, by removing static electricity remaining in a deep part inside a body of a massage recipient, getting the massage recipient into better physical conditions over the whole body in addition to a local part of the massage recipient. Two conductive portions arranged to be separated from each other, the conductive portions being capable of transmitting electricity to each other, and a discharge path disposed in one of the conductive portions, the discharge path being capable of discharging electricity to an exterior of the device.

20 Claims, 5 Drawing Sheets

MASSAGE DEVICE

TECHNICAL FIELD

The present invention relates to a massage device particularly capable of vitalizing a local part of a body and the whole body at a cellular level.

BACKGROUND ART

Various massage devices are roughly divided into three types and classified into a pressing type massage device, a permanent magnet type massage device, and an electricity-applying type massage device. A representative pressing type massage device includes a shiatsu style device having a leading end portion which is rounded such as a spherical body. This is a massage device that gets a massage recipient into better physical conditions by performing a centripetal practice of applying the leading end portion onto a local part, pressing, and moving by a practitioner or the massage recipient himself/herself, and thereby, removing waste inside the body, improving blood circulation, and also facilitating a flow of lymph.

A permanent magnet type massage device in which magnetism of a permanent magnet is utilized is a massage device that gets a massage recipient into better physical conditions by moving the permanent magnet while applying the permanent magnet onto a local part or keeping the permanent magnet away from the local part so that magnetism affects tissues of a body, and thereby, removing waste inside the body, improving blood circulation, and also facilitating a flow of lymph.

Further, an electricity-applying type massage device is newly born. For example, an electricity-applying type massage device shown in Patent Literature 1 is a massage device that removes waste inside a body, improves blood circulation, and also facilitates a flow of lymph by generating magnetic force lines to be changed into a pulsed shape by adding magnetism of an electromagnet to magnetism of a permanent magnet, and applying the magnetic force lines to an affected part.

CITATION LIST

Patent Literature

PATENT LITERATURE 1: JP S51-110665 A (Page 1, FIG. 1)

PATENT LITERATURE 2: JP 2020-168060 A

SUMMARY OF INVENTION

Technical Problem

Any of the pressing type massage device, the permanent magnet type massage device, and the electricity-applying type massage device described above is proved to be capable of getting the massage recipient into better physical conditions by effectively stimulating the local part of the body, removing waste in the vicinity of the local part, improving blood circulation, and also facilitating a flow of lymph. However, although there are massage effects in the local part and the vicinity of the local part, the body is not fundamentally improved from the inside of the body by these massage operations. Therefore, the applicant continued research for many years, and as a result, found that it is possible to get a person into better physical conditions over the whole body in addition to a local part by removing static electricity inside the body or on a surface outside the body, and completed the technique of removing the static electricity inside the body or on the surface outside the body (Patent Literature 2).

The inventor further evolved the technique shown in Patent Literature 2, and succeeded in powerfully removing static electricity remaining in a deep part inside the body.

An object of the present invention is to provide an extremely new massage device capable of, by removing static electricity remaining in a deep part inside a body of a massage recipient, getting the massage recipient into better physical conditions over the whole body in addition to a local part of the massage recipient.

Solution to Problem

In order to solve the foregoing problem, a massage device according to the present invention is a massage device including two conductive portions arranged to be separated from each other, the conductive portions being capable of transmitting electricity to each other, and discharge means disposed in one of the conductive portions, the discharge means being capable of discharging electricity to an exterior. According to the features of the present invention, electric currents flowing from the conductive portion positioned on the massage recipient side flow to the exterior via the other conductive portion by the discharge means. Thus, it is possible to reliably and voluminously remove static electricity charged inside a body of a massage recipient.

It may be preferable that the conductive portions are capable of transmitting electricity to each other by electricity transmission with atmospheric discharge. According to this preferable configuration, the so-called atmospheric discharge between the conductive portions has an operation of instantaneously vanishing a large voltage gradient at once. The contactless discharge temporarily increases a flow of electric charge from one of the conductive portions to the other conductive portion, and this electric charge efficiently flows to the exterior by the discharge means.

It may be preferable that at least one of conductive terminals respectively provided in the conductive portions is configured oscillably so that the conductive terminals are temporarily brought close to or brought into contact with each other by movement of the massage device. According to this preferable configuration, it is possible to control an electricity transmission amount in response to a state of the massage recipient by adjusting a moving velocity, etc. of the massage device by a practitioner. In addition, at a time point when a potential difference between the massage recipient side and the practitioner side becomes large, the electricity transmission is temporarily generated by the atmospheric discharge between the conductive terminals. Thus, the static electricity charged in the massage recipient does not always influence the practitioner, and it is possible to minimize a harmful influence on health of the practitioner.

It may be preferable that in a conductive circuit that enables the electricity transmission between the conductive portions, conductive wires each of which has a conductive terminal at a leading end respectively extend from both the conductive portions, and the conductive terminals are arranged to be separated from each other so that atmospheric discharge is capable of being generated. According to this preferable configuration, a change in a separation distance between the conductive terminals is large, and it is possible to control the electricity transmission amount in response to the state of the massage recipient by adjusting the moving velocity, etc. of the massage device.

It may be preferable that a plurality of conductive wires each of which has a conductive terminal at a leading end are provided to extend at least from one side. According to this preferable configuration, it is possible to ensure an amount of transmitted electric currents by using relatively-thin and flexible conductive wires.

It may be preferable that at least one of the conductive wires each of which has the conductive terminal at the leading end is formed by a spiral conductive wire. According to this preferable configuration, the conductive wire is formed in a spiral shape. Thus, it is possible to substantially extend a length of the conductive wire itself, and make the conductive wire also function as an electric resistance (prevention of overcurrent).

It may be preferable a permanent magnet is arranged at least in the vicinity of the conductive portion on the side to be applied to a body of a massage recipient. According to this preferable configuration, the Lorentz force by the permanent magnet is generated on the massage recipient side due to movement of the massage device on the surface outside the body of the massage recipient. That is, the permanent magnet facilitates movement of the electric charge inside and outside the body of the massage recipient, and the electric charge is more easily taken in by the conductive portions.

DESCRIPTION OF EMBODIMENTS

Figure 1:
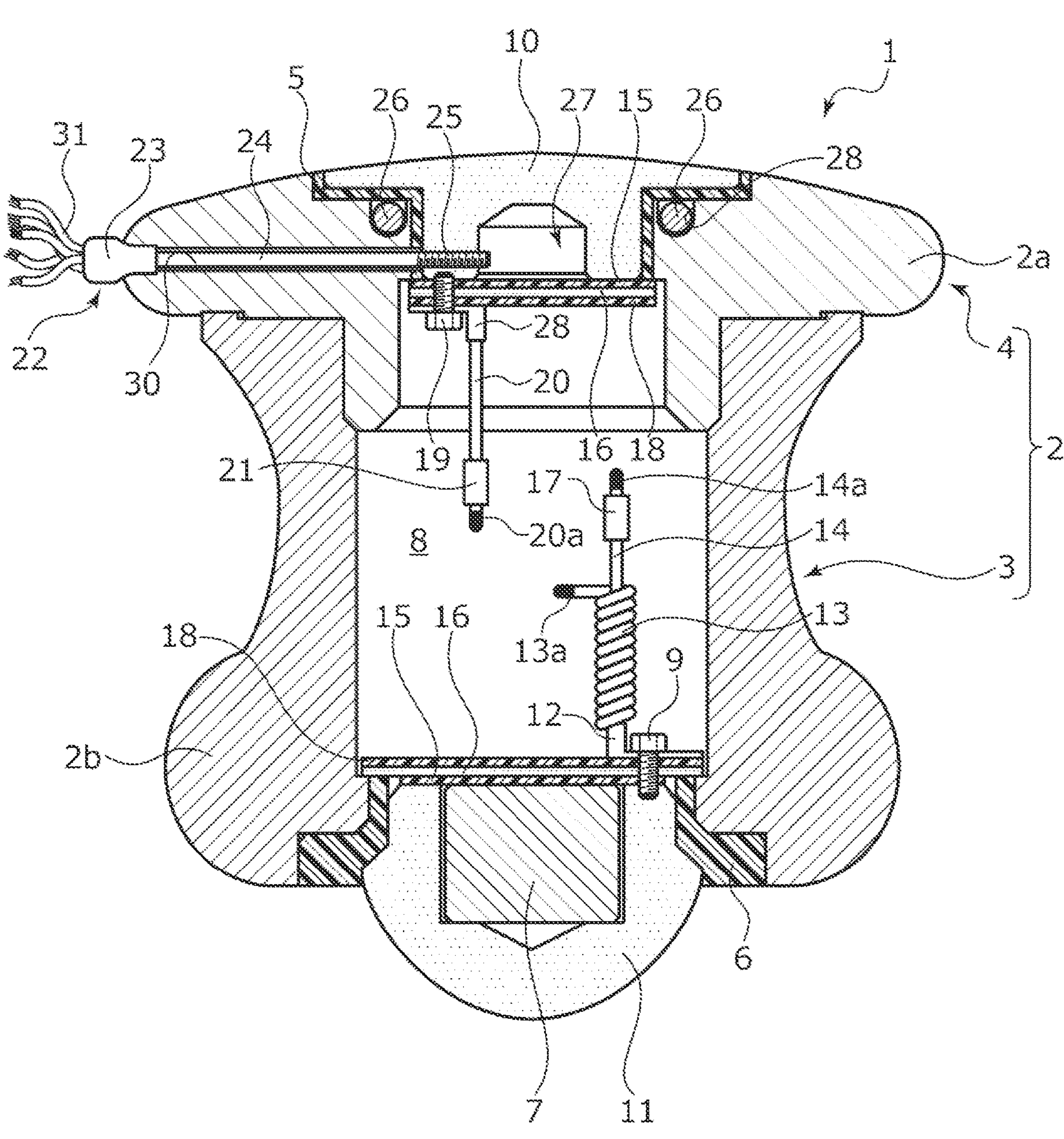
FIG. 1 is a sectional view illustrating a massage device according to an embodiment of the prevent invention.

A mode for carrying out a massage device according to the present invention will be described below based on an embodiment.

Embodiment

A massage device according to an embodiment of the present invention will be described with reference to FIGS. 1 to 5.

A massage device 1 is mainly configured by an exterior portion 2 to be described in detail later, a conductive circuit formed inside the exterior portion 2, a permanent magnet 7, and conductive end portions 10, 11 disposed in both end portions, the conductive end portions functioning as conductive portions.

The exterior portion 2 is formed in a substantially circular shape in a top view and has expanded portions 2*a*, 2*b* expanded outward in an upper portion and a lower portion in a side view. The exterior portion 2 has a constricted central portion in the up and down direction, and has a rounded shape as a whole, so as to be more easily gripped by a practitioner. It is noted that a maximum outer diameter of the expanded portion 2*b* on the lower side is formed to be smaller than a maximum outer diameter of the expanded portion 2*a* on the upper side, so that anti-slip for fingers of the practitioner is provided, and the expanded portion 2*b* is less easily brought into contact with a massage recipient.

The exterior portion 2 has a space 8 passing through up and down in the center, and includes a base member 3 having the conductive end portion 11 to be applied onto a body of the massage recipient, and an upper member 4 having the conductive end portion 10 to be held by the practitioner and abutted with a palm of the practitioner on the upper side of the base member 3. It is noted that in the embodiment, although the air exists in the space 8, a gas, a liquid, etc. which is suitable for contactless discharge can be variously selected.

In order to improve weightiness and operation stability, the base member 3 is made of a material such as aluminum or an aluminum alloy, and a columnar aluminum ingot material is integrally formed by cutting machining, molding, etc. A surface of this base member 3 does not have a conductive property by alumite processing, etc. It is noted that in a case where the weightiness is omitted, the base member 3 may be made of a wood material or synthetic resin. In a case of the present embodiment, the base member 3 has the conductive property. Thus, an insulating body 6 is provided to be respectively interposed between the conductive end portion 11 and the base member 3 in an insulated state.

In more detail, the upper member 4 functions as a grip portion, and includes the conductive end portion 10 made of a material such as a metal including chrome steel, iron, nickel, cobalt, manganese, gadolinium, terbium, or stainless steel, or an alloy of these metals in a recessed portion formed in the center via an insulating body 5. In particular, chrome steel is extremely favorable for having high corrosion resistance against sebum, sweat, etc. As illustrated in the figure, although the upper member 4 and the base member 3 are fixed by recess-projection fitting, fixing may be any of screwing, bonding, fitting, etc.

The conductive end portion 11 includes a space inside, and is fixed to an opening of a lower portion of the base member 3 via the insulating body 6 serving as an annular sleeve which is made of synthetic resin such as polyacetal.

In the space inside the conductive end portion 11, the permanent magnet 7 serving as a neodymium magnet, a ferrite magnet, an alnico magnet, etc. is arranged to be incapable of moving. In addition, the conductive end portion 11 is made of a material such as a metal including chrome steel, iron, nickel, cobalt, manganese, gadolinium, terbium, or stainless steel, or an alloy of these metals, and has the conductive property, and a magnetic force of the permanent magnet 7 is more easily transmitted to an exterior.

On upper surfaces of the conductive end portion 11 and the permanent magnet 7, a metal plate 15 made of a metal having a high conductive property such as copper, the metal plate being sandwiched by disc-shaped plates 16, 18 made of synthetic resin such as polyethylene terephthalate is arranged.

A through hole is formed downward in the metal plate 15 and the plates 16, 18, and a screw 9 is screwed into a female screw portion of the conductive end portion 11 on the lower side via this through hole. Further, a terminal portion 12 projecting upward by lancing processing is sandwiched between the screw 9 and the plate 18. A conductive wire 14 whose surface is insulated, the conductive wire having a conductive terminal 14*a* at a leading end is attached to this terminal portion 12, so that electricity transmission from the conductive end portion 11 to an interior of the space 8 is enabled. Similarly, a conductive wire 13 whose surface is insulated, the conductive wire having a conductive terminal 13*a* at a leading end extends in a spiral shape in the space 8, so that the electricity transmission from the conductive end portion 11 to the interior of the space 8 is enabled.

The conductive wire 13 extending in a spiral shape in the space 8 and enabling the electricity transmission from the conductive end portion 11 to the interior of the space 8 is wound around the conductive wire 14 in the present embodiment. The conductive wire 13 and the conductive wire 14 are connected to the terminal portion 12 to be capable of transmitting electricity, and each of the conductive wires configures an independent conductive circuit respectively to the different conductive terminal 13*a*, 14*a*. Thus, a large amount of electric currents can flow by the plurality of conductive wires. Further, the conductive wire 13 enabling the electricity transmission from the conductive end portion 11 to the interior of the space 8 is formed in a spiral shape. Thus, it is possible to make a length of the conductive wire 13 itself longer than the conductive wire 14, and make the conductive wire also function as an electric resistance (prevention of overcurrent).

Before the conductive terminal 14*a* of the conductive wire 14 extending upward, a heater 17 serving as a resistor is provided in an upper portion in order to convert part of the electric currents into heat and prevent overcurrent, so that part of the electric currents flowing through the conductive wire 14 can be diffused as thermal energy. In addition, the conductive wire 14 extending upward is formed in a linear shape and hence has flexibility, so that the conductive terminal 14*a* is oscillable in the right and left direction and in the front and rear direction by movement and vibration of the massage device 1.

In order to improve the weightiness and stability, the base member 3 is made of a material such as aluminum or an aluminum alloy, and a columnar aluminum ingot material is integrally formed by cutting machining, molding, etc. The surface of this base member 3 does not have the conductive property by alumite processing, etc. It is noted that in a case where the weightiness is omitted, the base member 3 may be made of a wood material or synthetic resin. In a case of the present embodiment, the upper member 4 has the conductive property. Thus, the insulating body 5 is provided to be respectively interposed between the conductive end portion 10 and the upper member 4 in an insulated state.

As described above, the upper member 4 functions as the grip portion, and includes the conductive end portion 10 made of a material such as a metal including chrome steel, iron, nickel, cobalt, manganese, gadolinium, terbium, or stainless steel, or an alloy of these metals in the recessed portion formed in the center via the insulating body 5 serving as an annular sleeve which is made of synthetic resin such as polyacetal.

In the upper member 4 positioned on the lower side of the insulating body 5 serving as an annular sleeve, as in FIG. 4 to be described later, six spherical permanent magnets 26, 26, . . . are arranged at equal intervals in the circumferential direction. The permanent magnet 26 is configured by a neodymium magnet, a ferrite magnet, an alnico magnet, etc., and arranged to be incapable of moving. These permanent magnets 26, 26, . . . are arranged at equal intervals on the outside of the conductive end portion 10 via the insulating body 5 serving as an annular sleeve which is made of synthetic resin such as polyacetal. Further, in a side portion of the upper member 4, an opening hole 30 passes through the insulating body 5, extends to a female screw hole formed in the conductive end portion 10, and extends to a space 27 formed inside the conductive end portion 10.

Further, from the side portion of the upper member 4, a conductive wire 24 of discharge means 22 is inserted into the opening hole 30 passing through the insulating body 5. A male screw 25 formed at a leading end of the conductive wire 24 is screwed in and fixed to a female screw hole formed in the conductive end portion 10. This discharge means 22 extends to the space 27 formed inside the conductive end portion 10, has a discharge wire portion 31 at a rear end, and is fixed to the opening hole 30 via an insulating cap 23. Therefore, regarding the discharge wire portion 31 and the conductive wire 24, electricity transmission with the conductive end portion 10 is enabled without contact with the upper member 4.

On a lower surface of the conductive end portion 10, a metal plate 15 made of a metal having a high conductive property such as copper, the metal plate being sandwiched by disc-shaped plates 16, 18 made of synthetic resin such as polyethylene terephthalate is arranged.

A through hole is formed downward in the metal plate 15 and the plates 16, 18, and a screw 19 is screwed into a female screw portion of the conductive end portion 10 on the upper side via this through hole. Further, a terminal portion 28 projecting upward by lancing processing is sandwiched between the screw 19 and the plate 18. A conductive wire 20 whose surface is insulated, the conductive wire having a conductive terminal 20*a* at a leading end is attached to this terminal portion 28, so that electricity transmission from the interior of the space 8 to the conductive end portion 10 is enabled. Since the conductive wire 20 has flexibility, the conductive terminal 20*a* serving as a free end portion is oscillable. Further, a diode 21 is provided, and the electric current direction is set and rectified by this diode 21.

The conductive terminal 20*a* and the conductive terminals 13*a*, 14*a* are arranged closely in the space 8. Thereby, via these conductive wires 13, 14, the heater 17, the diode 21, and the conductive wire 20, the conductive end portion 11 and the conductive end portion 10 can transmit electricity to each other by a conductive circuit including atmospheric discharge.

In more detail, the conductive terminal 20*a* and the conductive terminals 13*a*, 14*a* are normally not in contact with each other. Thus, at the time of not using the massage device 1, the conductive end portion 11 and the conductive end portion 10 are in a non-electricity transmission state. At the time of using the massage device 1, by movement (practice) of the massage device 1, a voltage difference starts to be generated gradually between the conductive end portion 11 and the conductive end portion 10, and further, the conductive terminal 20*a* and the conductive terminals 13*a*, 14*a* are temporally brought close to each other with oscillation, etc., in the structure. Thus, the electricity transmission with discharge due to the voltage difference is generated between the conductive terminal 20*a* and the conductive terminals 13*a*, 14*a*.

Figure 2:
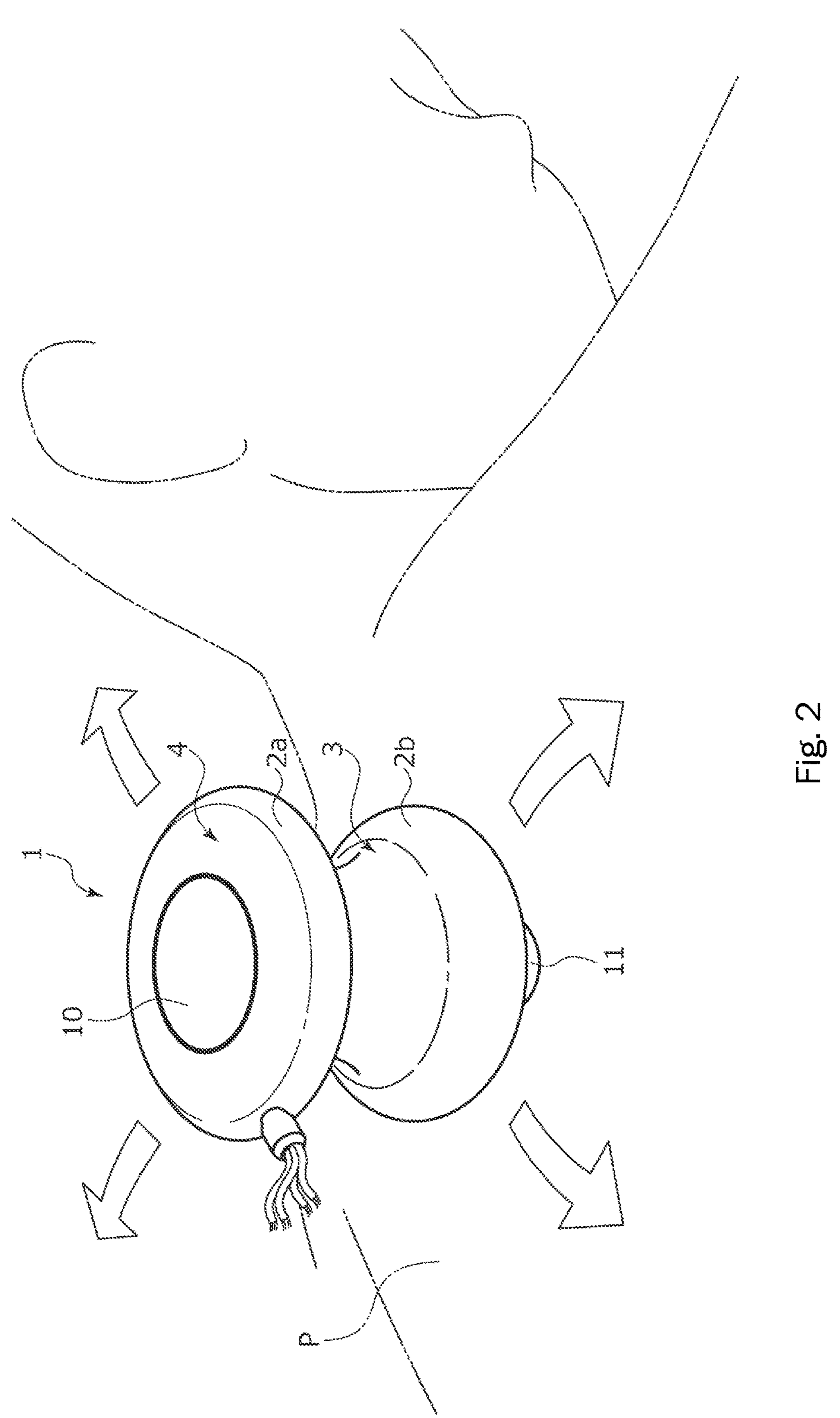
FIG. 2 is a view illustrating a practice mode in which the massage device is used.

Next, a method of using the massage device 1 and operations thereof will be described. As illustrated in FIG. 2, a practitioner S grips the upper member 4 side of the massage device 1, and performs a so-called centripetal practice or a practice with reciprocating movement of sliding the conductive end portion 11 on the lower side of the base member 3 on a surface outside a body of a massage recipient P.

It is known that since a human body utilizes a flow of electricity for brain and neural transmission in an activity, static electricity charged inside the body or on the surface outside the body harmfully influences the flow of electricity to be used for this activity. In addition, it is said that cells are also charged with electricity by activities of mitochondria, etc. Therefore, the massage device 1 of the present invention realizes improvement of functions of a human body by, in addition to a function of improving blood circulation by a centripetal practice, removing static electricity from the human body of the massage recipient P charged with a lot of static electricity, that is, changing positive and negative electric charge accumulated inside the body into a stable state. A mechanism thereof will be described in detail below.

It is noted that as a condition under which an effect of the massage device 1 becomes prominent, at the time of practice, the massage recipient P is required to be charged with electricity biasedly to positive polarity, and for the practitioner S, positive and negative electric charge are required to be stabilized. Therefore, at the time of practice, a potential difference is generated relatively between both the massage recipient P and the practitioner S.

As described above, the conductive terminal 20*a* and the conductive terminals 13*a*, 14*a* are normally not in contact with each other. Thus, at the time of not using the massage device 1, the conductive end portion 11 and the conductive end portion 10 are in a non-electricity transmission state. At the time of practice, as in FIG. 2, the practitioner S grips the upper member 4 side of the massage device 1, and slides the conductive end portion 11 on the lower side of the base member 3 on the surface outside the body of the massage recipient P. The conductive wires 13, 14 serving as part of the conductive circuit which extends from the conductive end portion 11 are oscillable on the upper side, and in this embodiment, the conductive wire 20 is also oscillable.

Figure 3:
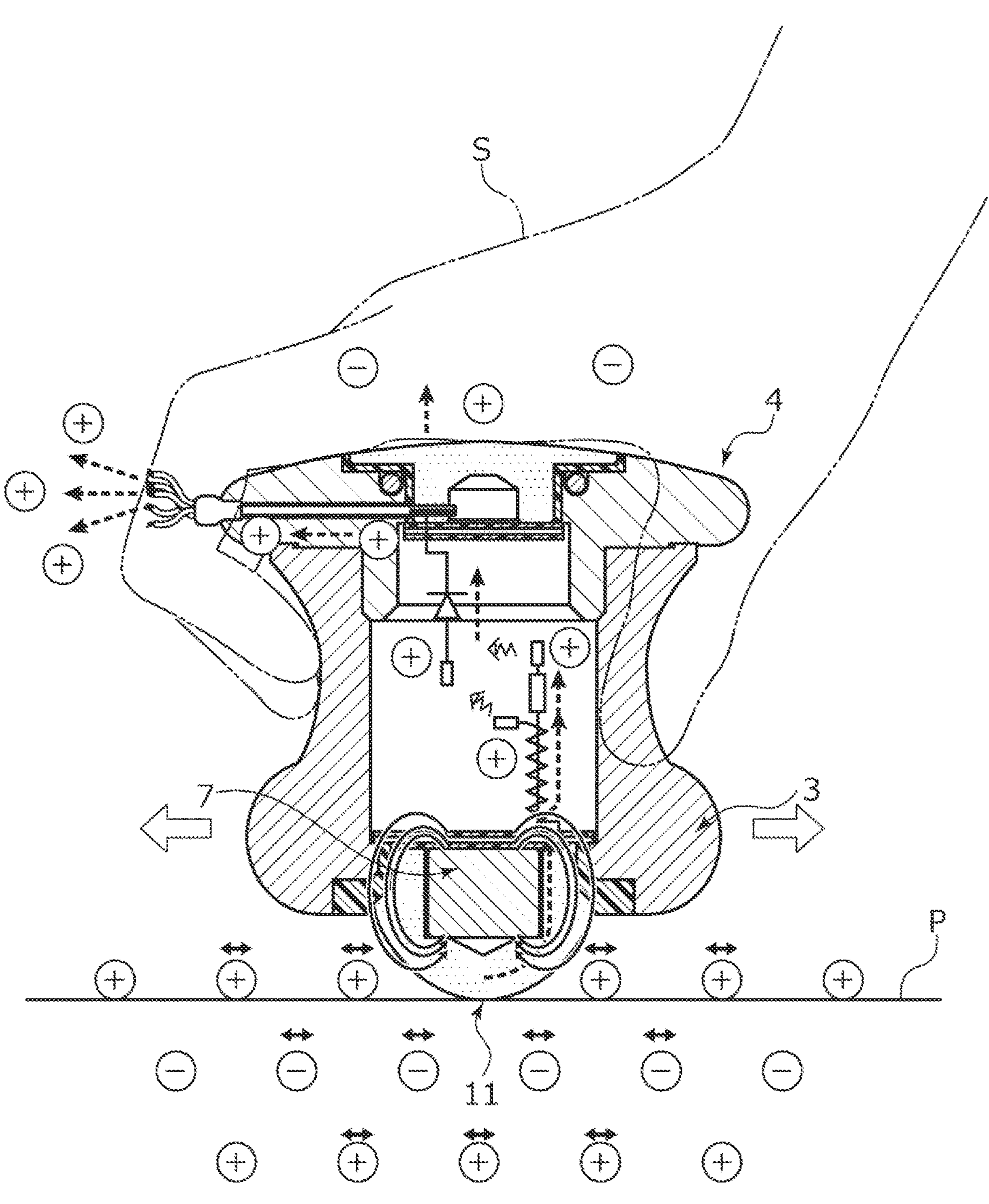
FIG. 3 is an image view illustrating a state where static electricity inside a body of a massage recipient or on a surface outside the body is removed.

At the time of using the massage device 1, by the movement (practice) of the massage device 1, as illustrated in FIG. 3, a voltage difference starts to be generated gradually between the conductive end portion 11 and the conductive end portion 10, and further, the conductive terminal 20*a* and the conductive terminals 13*a*, 14*a* are temporally brought close to each other with oscillation, etc., in the structure. Thus, the electricity transmission with discharge due to the voltage difference generated between the conductive terminal 20*a* and the conductive terminals 13*a*, 14*a* is generated. At this time, it is thought that an extremely high potential difference temporarily exists between both the massage recipient P and the practitioner S. It is noted that the oscillation of the conductive wires is not necessarily required, and the conductive terminal 20*a* and the conductive terminals 13*a*, 14*a* may be installed closely to each other from the start.

In addition, regarding the temporary existence of a high potential difference between both the massage recipient P and the practitioner S, it is thought that gathering of the positive electric charge on the side in contact with the body of the massage recipient P and the opposite negative electric charge on the conductive end portion 10 side to be abutted with a hand of the practitioner S in a state of attracting each other, so-called induced charge is generated.

Leading end portions of the conductive terminals 20*a*, 13*a*, 14*a* have a thin and pointed shape, and the positive electric charge concentrates on the thin and pointed leading ends of the conductive terminals 13*a*, 14*a*. When a potential gradient (electric field) becomes strong between the leading ends of the conductive terminals 13*a*, 14*a* and the leading end of the conductive terminal 20*a* due to close gathering of the positive electric charge, ionization energy of the air is exceeded, and atmospheric discharge (flow of electric currents) is generated from the conductive terminals 13*a*, 14*a* toward the conductive terminal 20*a* close-by. This discharge phenomenon can be explained by a phenomenon that at a position before touching a door knob, discharge is accompanied from a finger momentarily. The discharge has an operation of instantaneously vanishing a large voltage gradient at once. The contactless atmospheric discharge enhances an effect of attracting a flow of electric charge.

By this atmospheric discharge, an electricity transmission state is momentarily generated between the massage recipient P and the practitioner S. At this time, by the potential difference described above between the body of the massage recipient P charged with electricity biasedly to the positive polarity and the practitioner S, electric currents are generated from the body of the massage recipient P charged with electricity biasedly to the positive polarity in the direction of the practitioner S. In such a way, in a case of the present embodiment, the conductive terminals 20*a*, 13*a*, 14*a* are configured to be temporarily brought close to each other, and it is also possible to control an electricity transmission amount in response to a state of the massage recipient by adjusting a moving velocity, etc. of the massage device by the practitioner.

By moving the negative electric charge from the body of the practitioner S to the body of the massage recipient P through the massage device 1 by this movement of the electric currents, the static electricity on the surface outside the body or inside the body of the massage recipient P is removed, and it is possible to improve disorderedness due to the static electricity. Such an operation of removing the static electricity can produce an effect of effectively improving the disorderedness due to the static electricity for a predetermined affected part by moving the massage device 1 on the surface outside the body of the massage recipient P and changing a position of the massage device 1.

By moving the negative electric charge from the body of the practitioner S to the body of the massage recipient P through the massage device 1 by the movement of the electric currents, the static electricity on the surface outside the body or inside the body of the massage recipient P is removed, and it is possible to improve the disorderedness due to the static electricity. However, there is a danger that a lot of positive electric charge enters the practitioner S from the massage recipient P. Therefore, in the present embodiment, as described above, from the side portion of the upper member 4, the conductive wire 24 of the discharge means 22 is inserted into the opening hole 30 passing through the insulating body 5 and the male screw 25 formed at the leading end of the conductive wire 24 is screwed in and fixed to the female screw hole formed in the conductive end portion 10. This discharge means 22 extends to the space 27 formed inside the conductive end portion 10, has the discharge wire portion 31 at the rear end, and is fixed to the opening hole 30 via the insulating cap 23. Therefore, regarding the discharge wire portion 31 and the conductive wire 24, the electricity transmission with the conductive end portion 10 is enabled without contact with the upper member 4. It is noted that the so-called atmospheric discharge between the conductive end portions 10, 11 has the operation of instantaneously vanishing a large voltage gradient at once. The contactless discharge temporarily increases the flow of electric charge from one of the conductive end portions to the other conductive end portion, and the electric charge having nowhere to go efficiently flows to the exterior by the discharge means 22.

Figure 4:
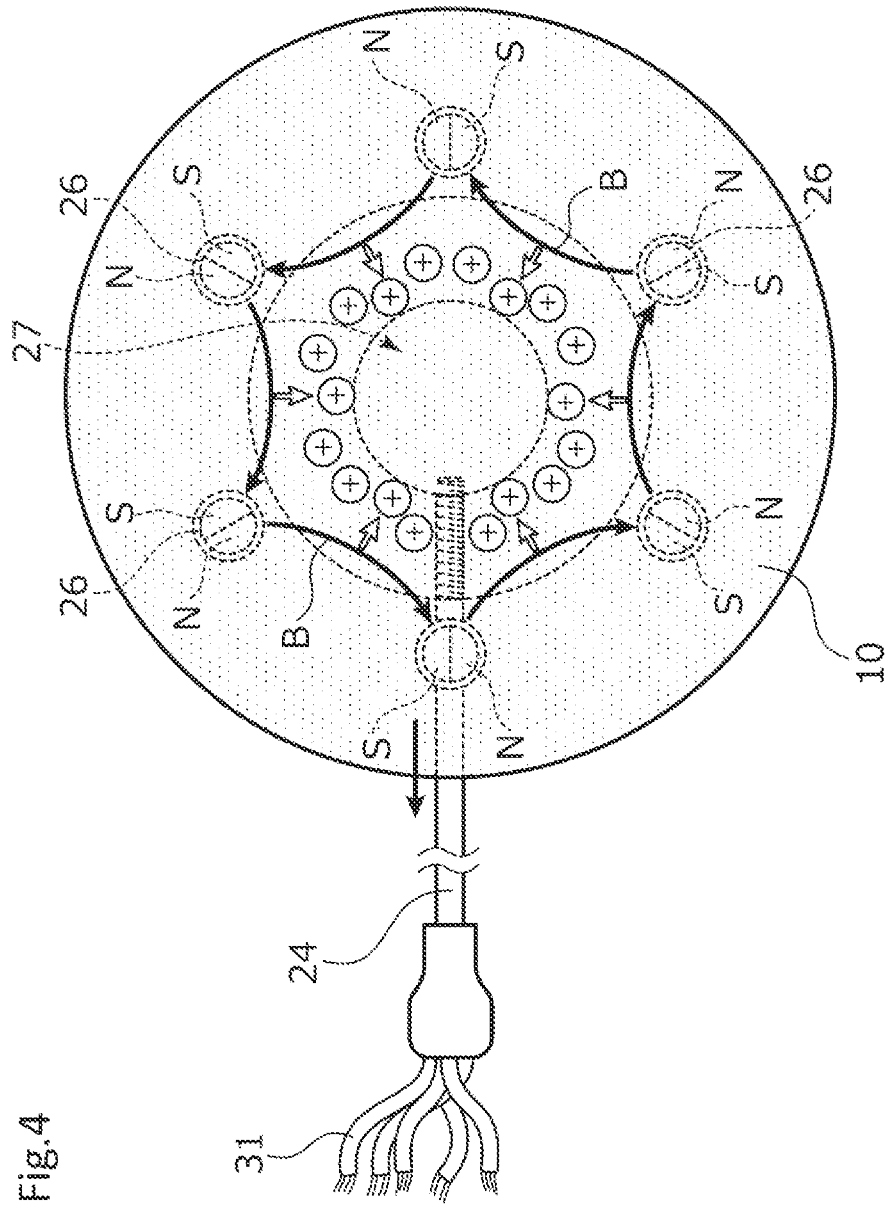
FIG. 4 is an image view explaining a mode in which positive electric charge is induced in the direction of a ground wire.
Figure 5:
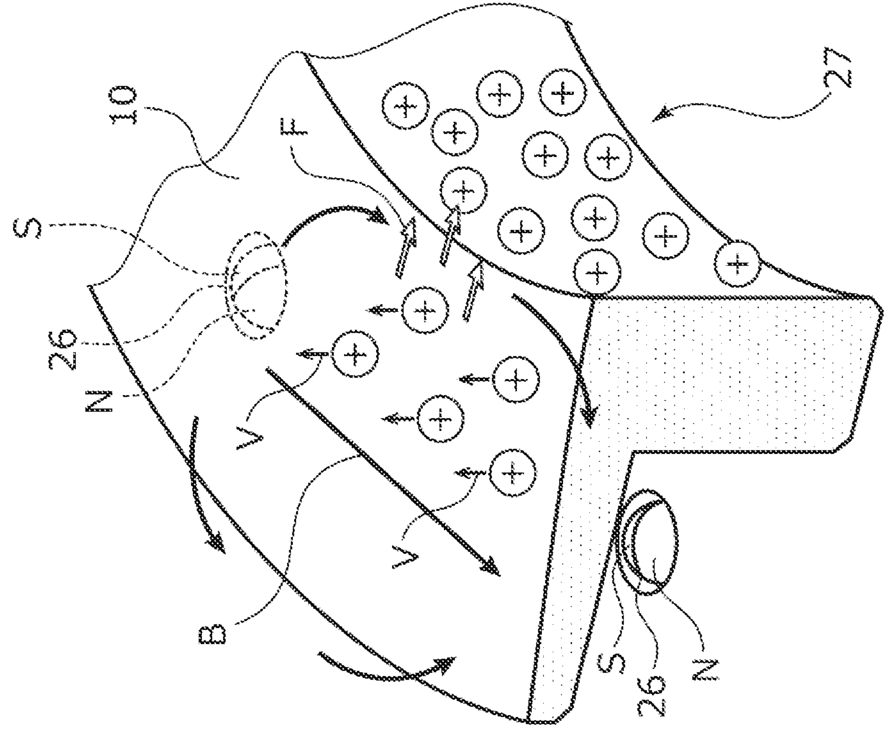
FIG. 5 is a perspective image view of major parts in FIG. 4.

As in FIG. 4, the six spherical permanent magnets 26, 26, . . . are arranged at equal intervals in the circumferential direction. The permanent magnet 26 is rotatably arranged to be incapable of moving in a semi-spherical recessed portion. With this configuration, as illustrated in FIGS. 4 and 5, a magnetic field B by magnetic poles N-S is generated in the circumferential direction. According to this structure, moving force is generated in each electric charge particle (positive electric charge) as explained in FIG. 5. That is, temporarily on the practitioner S side, although each electric charge particle (positive electric charge) tries to move upward from the massage recipient P through the conductive end portion 10 by velocity vector V, by the Lorentz force, that is, the existence of the magnetic field B, each electric charge particle moving by the velocity vector V receives a force F and is induced in the horizontal direction, so that movement to the practitioner S side is inhibited. Therefore, each electric charge particle accumulated in the conductive end portion 10 is induced by the male screw 25 and the conductive wire 24, and more easily discharged to the atmosphere from the discharge wire portion 31, so that it is possible to prevent the danger that a lot of positive electric charge enters the practitioner S from the massage recipient P. The discharge to the atmosphere from the discharge wire portion 31 is generated by the potential difference from the atmosphere as a phenomenon but can be generated by a potential difference from a cloth, a fabric, or other objects in a surrounding area. The discharge has the operation of instantaneously vanishing a large voltage gradient at once, and the contactless atmospheric discharge enhances the effect of attracting the flow of electric charge.

In addition, a state where the positive electric charge is biased in a human body can similarly be said as a state where there are a lot of positive reactive oxygen species, and there is a fear that the reactive oxygen species have a harmful influence such as oxidization of tissues of a body. The massage device 1 of the present invention detoxifies the reactive oxygen species by effectively removing the static electricity, that is, producing a proper balance with the negative electric charge, and exerts an extremely useful effect for health of the massage recipient P.

In addition, it is possible to knead the reactive oxygen species out as waste to the outside of the body through blood by a centripetal practice effect by the massage device 1 and by improving blood circulation and also facilitating a flow of lymph, it is possible to get the massage recipient into better physical conditions.

By the electricity transmission between the massage recipient P and the practitioner S, it is possible to remove the static electricity of not only the affected part of the massage recipient P but over the whole body. Thus, it is possible to facilitate vitalization at a cellular level and get the massage recipient P into better physical conditions over the whole body.

In addition, at the time of the electricity transmission between the massage recipient P and the practitioner S, part of the electric currents is converted into heat by the heater 17 of the conductive wire 14 and diffused as energy. Thus, it is possible to reduce an amount of the electric currents flowing to the practitioner S side, change a total value of the electric currents received by the practitioner S into a minute value, and minimize a harmful influence on health of the practitioner S. It is noted that there are effects such as a resistance by the atmospheric discharge and diffusion of part of the electric currents as energy also in the spiral-shaped conductive wire 13. Therefore, it is also possible to omit the heater 17 of the conductive wire 14.

The electric currents flowing through the conductive wire 20 are rectified by the diode 21 without returning to the side of the diode 21, and it is possible to effectively remove the static electricity inside the body and/or on the surface outside the body of the massage recipient P. In addition, if by any chance, in a case where the practitioner S is charged with more static electricity than the massage recipient P, the static electricity charged in the practitioner S does not harmfully influence the body of the massage recipient P.

In addition, as illustrated in FIG. 3, in a case where the permanent magnet 7 in which a N pole and a S pole are positioned on the top and the bottom is arranged inside the conductive end portion 11, movement of the electric charge is more activated. A magnetic flux of the permanent magnet 7 influences the inside of the body or the surface outside the body of the massage recipient P through the conductive end portion 11 having the conductive property, and by moving the conductive end portion 11 on the surface outside the body of the massage recipient P, the Lorentz force induced by the permanent magnet 7 is generated. In detail, a change in the magnetic field by movement of this permanent magnet 7 acts on the positive electric charge of the massage recipient P, and if the change in the magnetic field is reworded, a relative velocity vector is provided to the electric charge particles. Since the conductive end portion 11 is moved in the front and rear direction, the right and left direction, and the up and down direction with respect to the massage recipient P by the practitioner S, the electric charge particles are moved actively without restraint and the electric charge particles are more easily taken into the conductive end portion 11. At the time of using the massage device 1, by the movement (practice) of the massage device 1, as illustrated in FIG. 3, the voltage difference starts to be generated gradually between the conductive end portion 11 and the conductive end portion 10 touching the practitioner S, and further, the conductive terminal 20*a* and the conductive terminals 13*a*, 14*a* are temporally brought close to each other with oscillation, etc., in the structure. Thereby, the electricity transmission with discharge due to the voltage difference generated between the conductive terminal 20*a* and the conductive terminals 13*a*, 14*a* is generated. The negative electric charge flowing from the practitioner S or the discharge wire portion 31 of the discharge means 22 to the massage recipient P is led to the inside of the body or the surface outside the body, and over a wide range of the body of the massage recipient P, a proper balance with the negative electric charge is produced, and it is possible to promptly get the massage recipient P into better physical conditions over the whole body.

By the movement of the permanent magnet 7, in addition to active movement of the negative electric charge inside the body or on the surface outside the body as described above, movement of the positive electric charge inside and outside the body is also facilitated, the actively-moving positive electric charge is more easily taken into the conductive end portion 11 moved by the practice, and at the same time, the negative electric charge is efficiently sent from the practitioner S side to the massage recipient P.

In addition, by the magnetism emitted from the permanent magnet 7 acting on the tissues of the body, waste inside the body is removed, blood circulation is improved, and a flow of lymph is also facilitated. Thus, massage effects are improved.

The embodiment of the present invention is described above with the drawings. However, specific configurations are not limited to the embodiment, and the present invention includes any changes and additions within the range not departing from the scope of the present invention.

For example, the embodiment describes that the practitioner S is in a state where the positive and negative electric charge are stabilized. However, the present invention is not limited to this. The state may be any of a state where although a lot of electric charge of the same polarity as the massage recipient P is accumulated in the practitioner S, more electric charge is accumulated in the massage recipient, and a state where a lot of electric charge of the opposite polarity to the massage recipient P is accumulated in a human body of the practitioner S.

In the embodiment described above, from the side portion of the upper member 4, the conductive wire 24 of the discharge means 22 is inserted into the opening hole 30 passing through the insulating body 5 and the male screw 25 formed at the leading end of the conductive wire 24 is screwed in and fixed to the female screw hole formed in the conductive end portion 10. However, the present invention is not limited to this structure, but the conductive wire 24 of the discharge means 22 may be taken out of the base member 3.

In the embodiment described above, the discharge to the atmosphere from the discharge wire portion 31 extending from the conductive wire 24 is enabled. However, it is clear that the conductive wire 24 may be extended and led to a grounded electrode (not shown).

In the embodiment described above, the electric currents flowing through the conductive wire 20 are rectified by the diode 21. However, it is also possible to omit the diode 21 in response to a health level of the massage recipient P. It is also possible to use a plurality of conductive wires 20 in response to the amount of the electric currents and in consideration to thickness of the wire.

In addition, in the present embodiment, the conductive wire 13 is wound around the conductive wire 14, the conductive wire 13 and the conductive wire 14 are connected to the terminal portion 12 to be capable of transmitting electricity, and each of the conductive wires configures the independent conductive circuit respectively to the different conductive terminal 13*a*, 14*a*. However, it is a design matter that various forms of conductive wires are independently provided to stand from the terminal portion 12 and the number of terminal portions is increased. The body of the practitioner may be a body of an animal other than human being but may be the practitioner himself/herself.

REFERENCE SIGNS LIST

1: Massage device
2: Exterior portion
2*a*, 2*b*: Expanded portion
3: Base member
4: Upper member
7: Permanent magnet
8: Space
10: Conductive end portion (conductive portion)
11: Conductive end portion (conductive portion)
13: Conductive wire
13*a*: Conductive terminal
14: Conductive wire
14*a*: Conductive terminal
16: Plate
17: Heater (resistor)
20: Conductive wire
20*a*: Conductive terminal
21: Diode
22: Discharge means
26: Permanent magnet
P: Massage recipient
S: Practitioner

The invention claimed is:

1. A massage device, comprising:

two conductive portions arranged to be separated from each other, the conductive portions being configured for transmitting electricity to each other; and a conductive circuit configured to enable transmitting electricity between the conductive portions, wherein a magnetic device is disposed near the conductive circuit, and a discharge device configured for discharging an electric charge flowing between the conductive portions to an exterior is disposed so as to extend to the side of the massage device, and wherein the conductive circuit has a circuit configured to redirect the electric charge flowing between the conductive portions by using the magnetic device and guiding the electric charge to the discharge device.

2. The massage device according to claim 1, wherein the conductive portions are capable of transmitting electricity to each other by electricity transmission with atmospheric discharge.

3. The massage device according to claim 2, wherein at least one of conductive terminals respectively provided in the conductive portions is configured oscillably so that the conductive terminals are temporarily brought close to or brought into contact with each other by movement of the massage device.

4. The massage device according to claim 2, wherein in a conductive circuit that enables electricity transmission between the conductive portions, conductive wires each of which has a conductive terminal at a leading end respectively extend from both the conductive portions, and the conductive terminals are arranged to be separated from each other so that atmospheric discharge is capable of being generated.

5. The massage device according to claim 2, wherein a plurality of conductive wires each of which has a conductive terminal at a leading end are provided to extend at least from one side.

6. The massage device according to claim 2, wherein at least one of the conductive wires each of which has the conductive terminal at the leading end is formed by a spiral conductive wire.

7. The massage device according to claim 2, wherein a permanent magnet is arranged at least in a vicinity of the conductive portion on the side to be applied to a body of a massage recipient.

8. The massage device according to claim 1, wherein at least one of conductive terminals respectively provided in the conductive portions is configured oscillably so that the conductive terminals are temporarily brought close to or brought into contact with each other by movement of the massage device.

9. The massage device according to claim 8, wherein in a conductive circuit that enables electricity transmission between the conductive portions, conductive wires each of which has a conductive terminal at a leading end respectively extend from both the conductive portions, and the conductive terminals are arranged to be separated from each other so that atmospheric discharge is capable of being generated.

10. The massage device according to claim 8, wherein a plurality of conductive wires each of which has a conductive terminal at a leading end are provided to extend at least from one side.

11. The massage device according to claim 8, wherein at least one of the conductive wires each of which has the conductive terminal at the leading end is formed by a spiral conductive wire.

12. The massage device according to claim 8, wherein a permanent magnet is arranged at least in a vicinity of the conductive portion on the side to be applied to a body of a massage recipient.

13. The massage device according to claim 1, wherein in a conductive circuit that enables electricity transmission between the conductive portions, conductive wires each of which has a conductive terminal at a leading end respectively extend from both the conductive portions, and the conductive terminals are arranged to be separated from each other so that atmospheric discharge is capable of being generated.

14. The massage device according to claim 13, wherein a plurality of conductive wires each of which has a conductive terminal at a leading end are provided to extend at least from one side.

15. The massage device according to claim 13, wherein at least one of the conductive wires each of which has the conductive terminal at the leading end is formed by a spiral conductive wire.

16. The massage device according to claim 13, wherein a permanent magnet is arranged at least in a vicinity of the conductive portion on the side to be applied to a body of a massage recipient.

17. The massage device according to claim 1, wherein a plurality of conductive wires each of which has a conductive terminal at a leading end are provided to extend at least from one side.

18. The massage device according to claim 17, wherein at least one of the conductive wires each of which has the conductive terminal at the leading end is formed by a spiral conductive wire.

19. The massage device according to claim 1, wherein at least one of the conductive wires each of which has the conductive terminal at the leading end is formed by a spiral conductive wire.

20. The massage device according to claim 1, wherein a permanent magnet is arranged at least in a vicinity of the conductive portion on the side to be applied to a body of a massage recipient.

* * * * *